US012796662B2

(12) United States Patent
Bolard

(10) Patent No.: US 12,796,662 B2
(45) Date of Patent: Nov. 17, 2026

(54) AUTOMATED FARMING INSTALLATION AND PROCESS

(71) Applicant: NASEKOMO B.V., Amsterdam (NL)

(72) Inventor: Marc Louis Raymond Bolard, Sofia (BG)

(73) Assignee: NASEKOMO B.V., Amsterdam (NL)

( * ) Notice: Subject to any disclaimer, the term of this patent is extended or adjusted under 35 U.S.C. 154(b) by 408 days.

(21) Appl. No.: 18/566,603

(22) PCT Filed: May 31, 2022

(86) PCT No.: PCT/EP2022/064830

§ 371 (c)(1),
(2) Date: Dec. 1, 2023

(87) PCT Pub. No.: WO2022/253862

PCT Pub. Date: Dec. 8, 2022

(65) Prior Publication Data

US 2024/0251768 A1 Aug. 1, 2024

(30) Foreign Application Priority Data

Jun. 3, 2021 (EP) .................................... 21177518

(51) Int. Cl.
*A01K 67/36* (2025.01)

(52) U.S. Cl.
CPC .................................. *A01K 67/36* (2025.01)

(58) Field of Classification Search
CPC ............................................ A01K 67/30–368
See application file for complete search history.

(56) References Cited

U.S. PATENT DOCUMENTS

| | | | | |
|---|---|---|---|---|
| 3,590,981 | A * | 7/1971 | Adrian | A01D 46/26 198/569 |
| 10,842,138 | B1 | 11/2020 | Lolley | |
| 11,311,003 | B2 * | 4/2022 | Yeh | A01K 67/30 |
| 2002/0144658 | A1 | 10/2002 | Holcombe et al. | |
| 2019/0166812 | A1 * | 6/2019 | Urbanski | A01K 67/30 |
| 2020/0253176 | A1 | 8/2020 | Fotiadis | |
| 2020/0323173 | A1 * | 10/2020 | Sabeg | A01K 67/368 |

(Continued)

FOREIGN PATENT DOCUMENTS

| | | | |
|---|---|---|---|
| CN | 209002649 | U | 6/2019 |
| CN | 110150234 | A | 8/2019 |
| CN | 110432229 | A | 11/2019 |

(Continued)

OTHER PUBLICATIONS

European Search Report and Opinion dated Nov. 5, 2021 regarding European Application No. EP4098114.

(Continued)

*Primary Examiner* — Gene O Crawford
*Assistant Examiner* — Keith R Campbell

(57) ABSTRACT

An automated farming installation (2) comprises a controller, one mobile workstation (6) controlled by the controller, and one work surface (3) able to support at least a load of substrate. The work surface (3) comprises a longitudinal continuous tank made by connection of at least two profiled tank portions, and the mobile workstation (6) is moved over a portion of the work surface to perform at least one sub-action controlled by the controller.

14 Claims, 6 Drawing Sheets

(56) References Cited

U.S. PATENT DOCUMENTS

2023/0363363 A1 * 11/2023 Lepek .................... A01K 67/30

FOREIGN PATENT DOCUMENTS

| | | | | | |
|---|---|---|---|---|---|
| CN | 110720436 | A | | 1/2020 | |
| CN | 111109204 | A | * | 5/2020 | ............. A01K 67/30 |
| CN | 112825820 | A | | 5/2021 | |
| EP | 3968476 | A1 | | 3/2022 | |
| KR | 200355794 | Y1 | | 7/2004 | |
| KR | 20170118294 | A | | 10/2017 | |
| KR | 20180004440 | A | | 1/2018 | |
| WO | WO2017007310 | A1 | | 1/2017 | |

OTHER PUBLICATIONS

International Search Report dated Sep. 2, 2022 regarding International Application No. PCT/EP2022/064830.

* cited by examiner

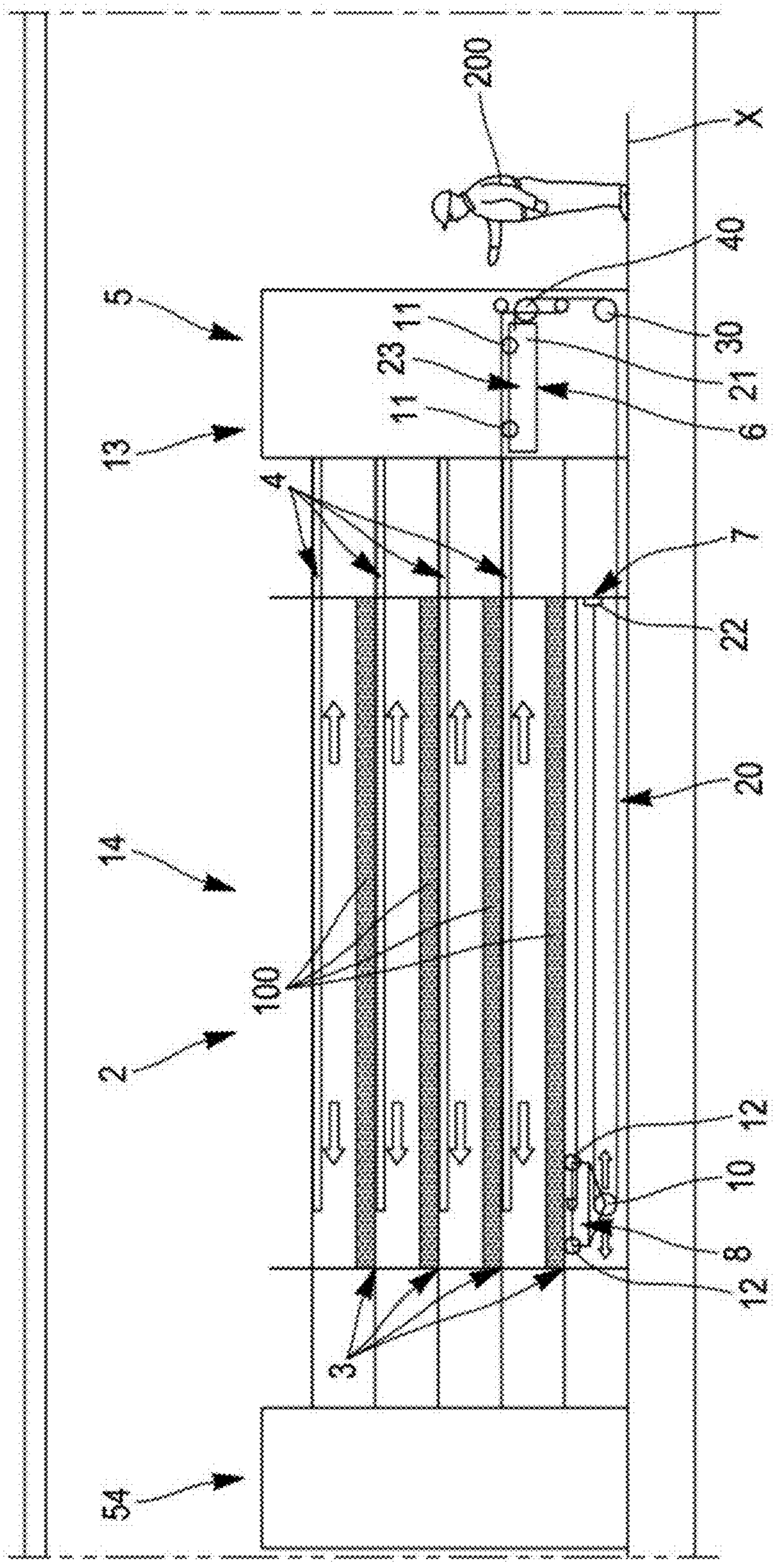
[Fig. 1]

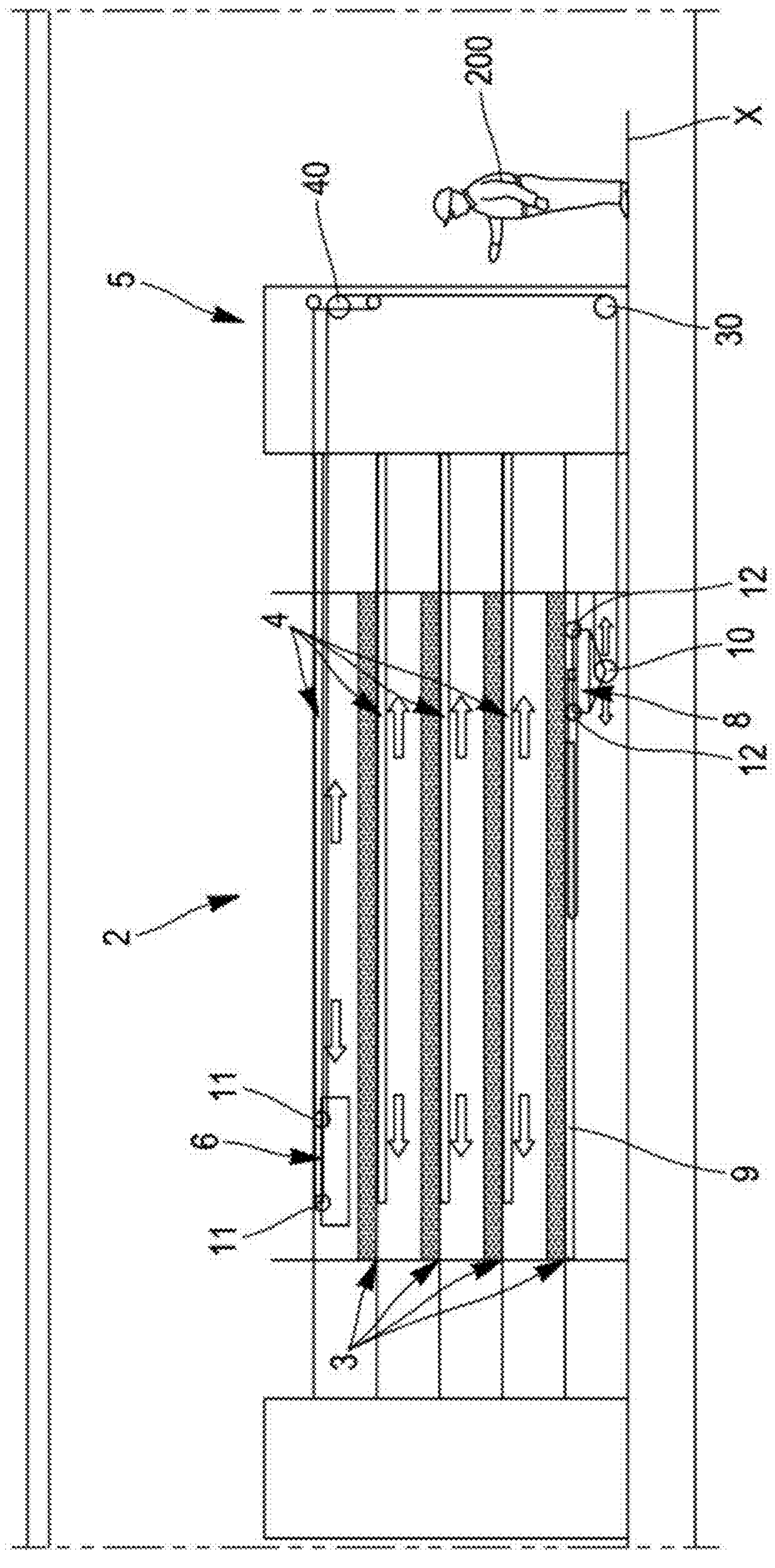
[Fig. 2]

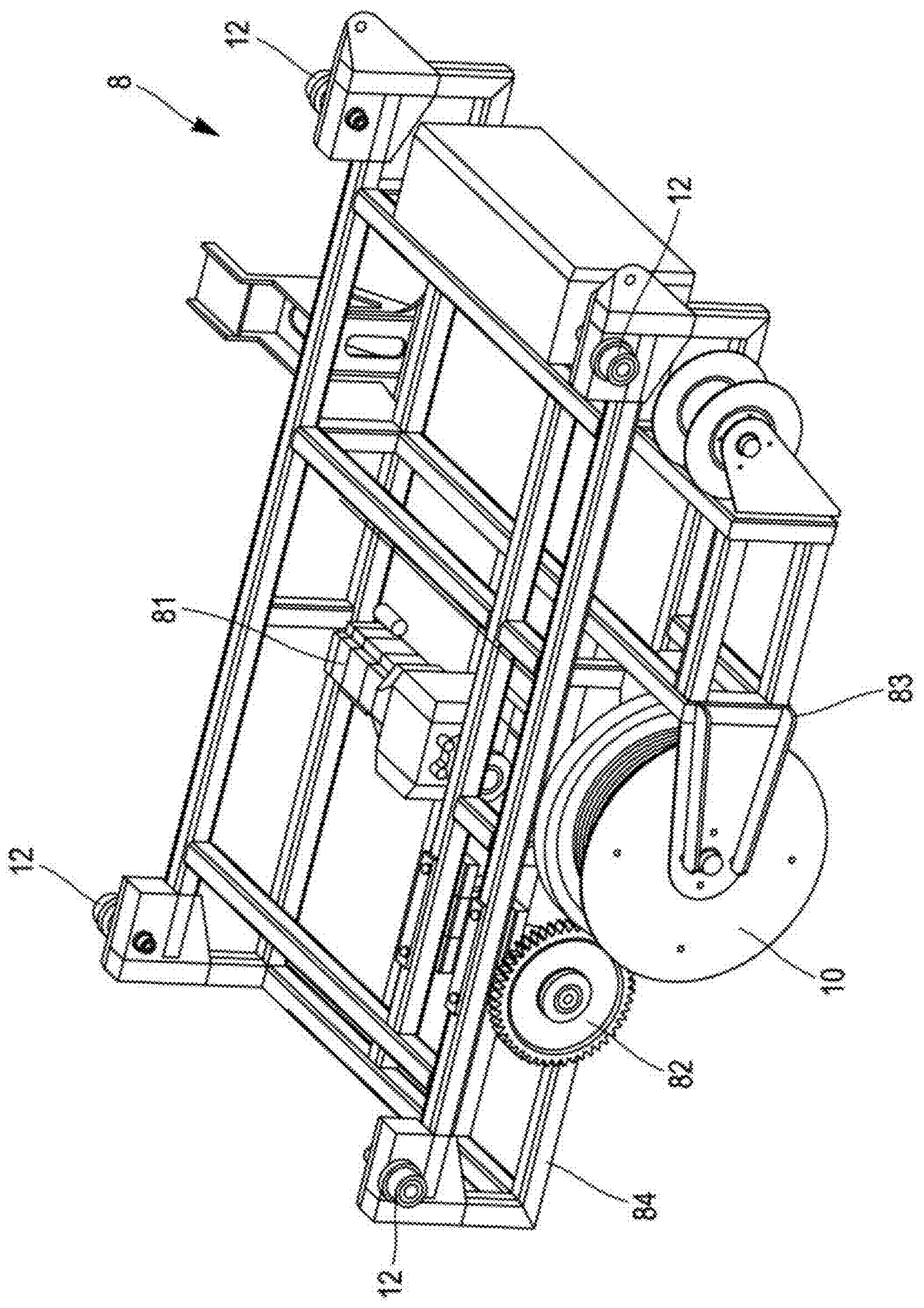
[Fig. 3]

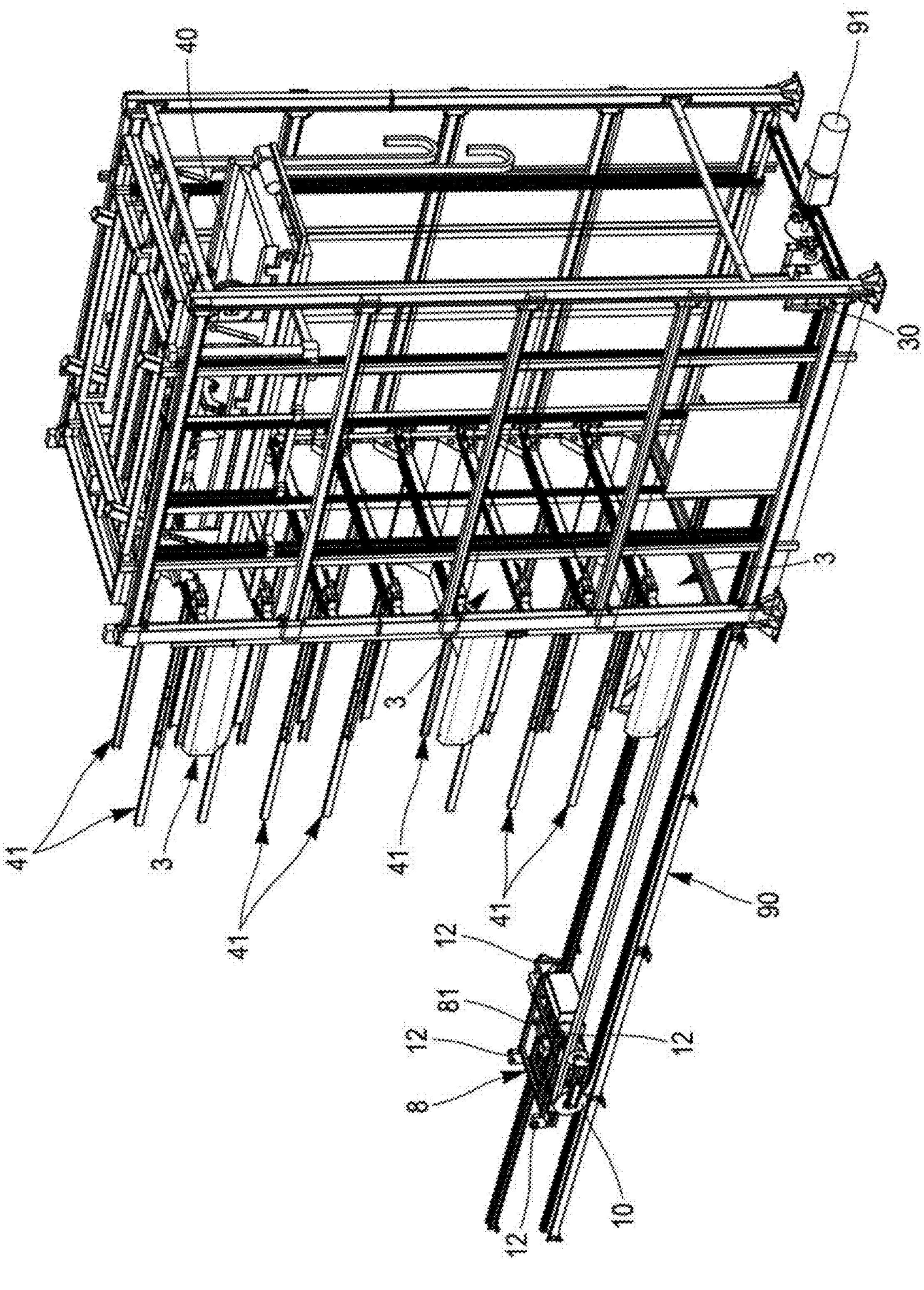
[Fig. 4]

[Fig. 5]
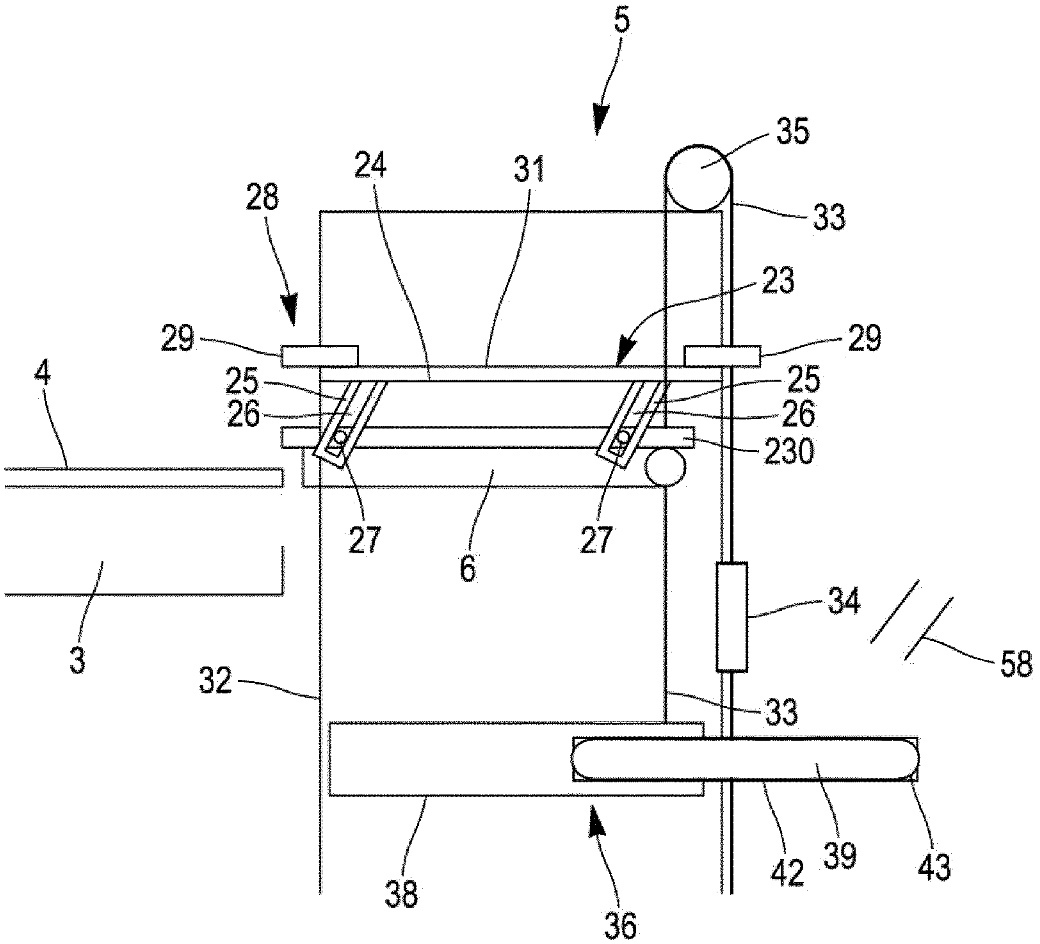

[Fig. 6]
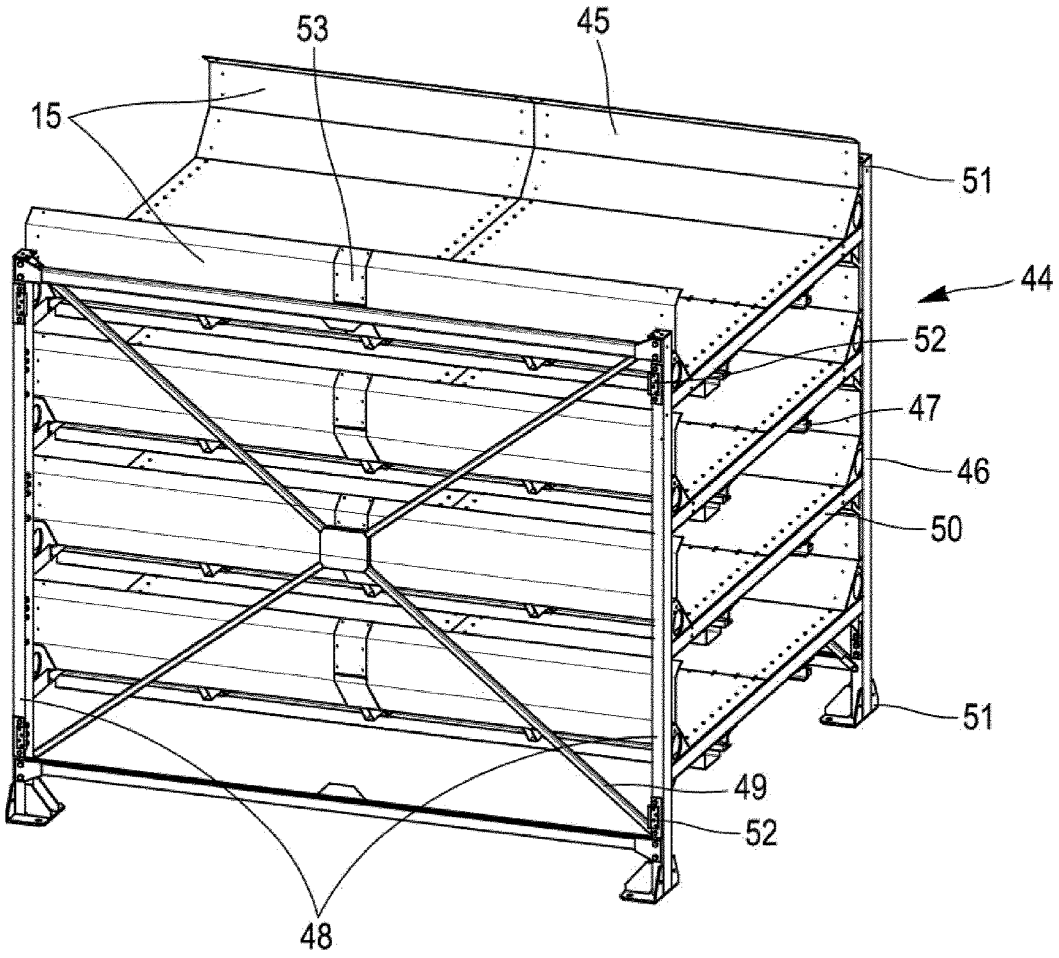
[Fig. 7]
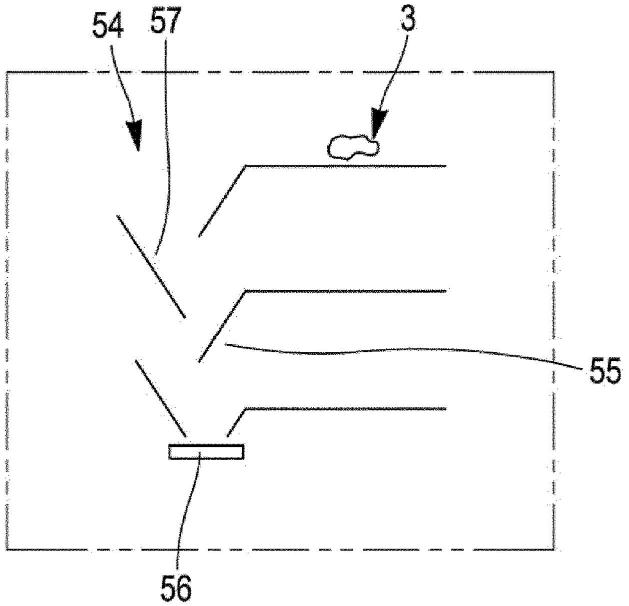

AUTOMATED FARMING INSTALLATION AND PROCESS

CROSS-REFERENCE TO RELATED APPLICATION

This application is a national stage application, filed under 35 U.S.C. § 371, of International Patent Application No. PCT/EP2022/064830, filed on May 31, 2022, which claims the priority to European application No. 21177518.4 filed on Jun. 3, 2021, the contents of which are incorporated by reference.

FIELD OF THE INVENTION

The present invention relates to the domain of automated farming, more precisely to an installation to effectively breed insects by the digestion of organic matter.

TECHNOLOGICAL BACKGROUND

The farming process relates to an installation for insect cultivation, for example larvae of BSF (i.e. Black Soldier Flies, Hermetia illucens), for example for the production of food (pet food in particular) and/or for the production of organic fertilizer.

Some insects efficiently convert organic waste matter into protein, which can be used for animal feeding. One solution to recycle these wasted biomasses is to set up a biological treatment by replicating at a large scale the natural process of organic waste treatment.

A whole cycle is made of 4 steps:

Step 1: Organic waste are collected from agricultural co-products for example, like breweries or ethanol plants;

Step 2: Insects are reared in a highly bio-secure environment and fed with the organic waste;

Step 3: Insects are collected from the remaining frass;

Step 4: On one hand, insects are dried, and a protein meal and a fatty fraction are separated and further processed into animal feed ingredients;

Step 5: On the other hand, the insect frass is extracted to be used as organic fertilizer for agricultural plantation.

Thus, the organic fertilizer is useful for vegetable farming, and the protein-rich meal and the insect oil are produced to feed animals.

Such process makes it possible to artificially reproduce the complete natural cycle of organic matter. Some pollution and waste of resources are avoided by replicating the whole natural cycle thanks to insect breeding.

Among the advantages of such process, the environmental impact is highly reduced, in terms of water consumption, agricultural land usage, feed consumption.

The above step 2 can be divided into two phases: A first phase comprises a maturation of insect eggs until the larvae hatch and grow for a few days, for example five days. A second aging phase in a substrate lasts for 4 to 15 days, for example 7 to 8 days, and results in mature larvae and frass. The present invention especially concerns this second aging phase.

Several attempts to automatize this phase of the cycle were developed, notably in Asia.

Document CN 110432229 A is an example where a module comprises a multi-level cage, each level having at least one breeding tank equipped with a track and at least one multifunctional mobile workstation, comprising a mobile seed drill for black soldier fly larvae, a rotation device which can operate a homogenization mechanism, a displacement mechanism, and a discharge scraper.

One of the problems targeted by this document is to control the temperature increase by mechanical action on the substrate.

Nevertheless, the size of such installation is limited by several factors.

One of the factors is the deployment and storing of the guiding chain for guiding flexible cables and/or pipelines to connect the mobile workstation to sources of energy, information, water, etc. Above several meters, especially above 7 meters, the size of the guiding chain cannot be stored by a simple winding.

The solution to this problem is described in the document EP20195904 titled “guiding chain carrier system”. The solution to manage this key issue is clearly described in this document.

Another factor of size limitation is the second aging phase installation itself and the process to manage the substrate during this aging phase.

On each breeding tank introduced by the prior art document CN 110432229, the system comprises two different equipment: one equipment for the spreading of insect feed and another equipment dedicated only to the seeding of insects.

Each level of breeding tank has its own mobile workstation.

The mobile workstation cannot perform all the actions requested to raise the larvae in ideal conditions. For instance, the operator must manually humidify the substrate.

Moreover, Document CN 110432229 A does not mention how the multifunctional mobile workstation is supplied with energy.

Having a single mobile workstation with all the necessary connection to supply energy and farming resources over a working surface longer than 7 meters is not possible with the use of one single workstation such as operated in the prior art.

The invention thus aims at optimizing such automated insect installation by highly increasing the working surface area covered by one single mobile workstation, improving the yield, reducing the space, equipment and manpower required, enhancing reliability and efficiency compared to existing installations.

Another benefit of the invention is to provide an installation of a size adapted to the needs with minimum investment and time.

Upstream of the device of the invention, a robotic seeding installation integrates insect larvae in a substrate which also provide the nutrients, for example coming from an organic waste.

The duration of the second aging phase in an installation depends on the age at which the larvae are introduced, how fast they grow and at what age harvesting is programmed. In the embodiment illustrated here after, these are 5-day-old larvae placed in the automated insect farming installation for 7 to 8 days growing period.

SUMMARY OF THE INVENTION

Thus, the invention relates to an automated farming installation comprising a controller, at least one mobile workstation controlled by the controller, and at least one work surface able to support at least a load of substrate, characterized in that the work surface comprises a longitudinal continuous tank made by connection of at least two profiled tank portions, and in that the mobile workstation is movable over a portion of the work surface to perform at least one sub-action controlled by the controller.

A work surface is a surface that can support a defined maximum quantity of a substrate product.

According to the invention, the substrate may comprise a mixture of non-nutritive fibers and nutriments which, itself, is mixed with insect larvae. As insect larvae consume the nutrients, they produce frass, so that, at some point in time, the substrate comprises a mixture of non-nutritive fibers, nutriments and frass which, itself, is mixed with insect larvae. Nutriments may comprise organic waste, seeds, plant sprouts and/or fungi.

According to the invention, an automated farming installation can be extended horizontally with the only limit of the speed of the mobile workstation combined with the number of actions to be performed over a limited period of time.

A mobile workstation is an operational device able to perform at least one action on a work surface. Repeating several sub-actions means that one main action (loading, applying one of the treatments, unloading, . . . ) is performed by the mobile workstation only on a portion of a work surface.

Depending on the action, the portion of the work surface that can be treated can be longer or shorter. To complete one action, sub-actions are repeated over different work surfaces by the same mobile workstation. Sub-actions of one main action can be performed over different portions of product. Sub-actions of one action are identical. In some cases, the portion of product to be treated is reduced to a sub-portion of the largest possible portion for one given action in order to target the corresponding work surface. In some other cases, one sub-action can be repeated on the same portion of product.

Thus, one single mobile station can cover a very large work surface. The only remaining limitation is the speed of the mobile workstation to perform one action for all the work surface compared to the maximum time allowed to perform this action. The whole second aging phase is usually limited to 8 days, maximum 15 days, so all the actions must be performed within this time limitation.

Another advantage of splitting one action into sub-actions is to perform one action only where and when it is requested.

Thanks to the invention, it is also possible to increase the thickness of the product to the maximum possible thickness according to the tank loading maximum capacity.

Thus, the invention makes it possible to increase yield of insects farming, as well as to decrease the footprint needed.

The entrance of the culture area is a position where the product can be loaded on the culture area.

The exit of the culture area is a position where the substrate can be recovered and disposed of.

According to various aspects, one or more of the following features may be implemented.

According to some embodiments, the invention relates to an automated farming installation further comprising a structural frame supporting the work surface, wherein the farming installation is provided as a plurality of assembled units, each unit comprising one of said tank portions and a structural frame portion, the structural frame portions being assembled to one another to provide the structural frame.

A unit can be assembled to one or to several other units. The work surface defined by the assembled units can be increased or reduced horizontally.

Units to assemble comprise a portion of the tank connectable to a portion of the tank of one or two other units to form a continued horizontal tank.

Thus, the size of the automated farming installation can be easily adapted to the quantity of substrate to be treated and to the space available to install the automated farming installation.

According to some embodiments, the invention relates to an automated farming installation further comprising at least one longitudinal guiding rail parallel to the longitudinal continuous tank and guiding a movement of the mobile workstation over the work surface.

According to some embodiments, the invention relates to an automated farming installation wherein each unit comprises a rail portion, the rail portions being assembled to provide the longitudinal guiding rail.

According to some embodiments, the invention relates to an automated farming installation comprising at least two work surfaces provided at at least two vertical levels, the one under the other.

According to some embodiments, the invention relates to an automated farming installation wherein at least one unit comprises at least the two vertical levels.

A unit can be assembled to one or to several other units. The work surface defined by the assembled units can be increased or reduced vertically.

A unit can comprise several portions of tank one above the other, to form several levels of work surfaces.

Thus, the size of the automated farming installation can be easily adapted to the quantity of substrate to be treated and to the space available to install the automated farming installation.

The vertical frame portions comprise, for example, vertical tubes installed on each lateral side of each unit, one end can be attached for example to a unit above, the other end of the tubes extends below the tank for assembly, for instance, to a unit below. In the case of the bottommost module, the other end of the tubes can also be placed on the ground. The tank of each unit may be fixed to its vertical frame portion.

Units to assemble can comprise, at the extremity of vertical tubes, means to fix a unit to assemble above another unit to assemble and to support at least the weight of several units.

Thus, it is possible to have the tank of the lowest unit above the ground, easing the cleaning under the tank.

Thus, it is also possible to have several levels of units one above the other. The empty space between the unit to assemble and the ground also eases maintenance.

Also, the said empty space can be used to store supplies pipelines and cables without using any additional footprint.

It is also possible to add several units above one unit.

In fact, to have more substrate on the work surface may request reinforcements based on the ground along both lateral edges of the work surface.

Thus, the quantity of substrate treated per unit of available ground space area is increased.

According to some embodiments, the invention relates to an automated farming installation wherein at least one unit is adapted to support at least an overlying unit.

According to some embodiments, the invention relates to an automated farming installation further comprising a lift system comprising:

A static structure,

A vertically movable part, vertically movable with respect to the static structure, and adapted to receive, to support and to deliver the mobile workstation.

According to some embodiments, the invention relates to an automated farming installation wherein the lift system further comprises a second vertically movable part, vertically movable with respect to the static structure.

According to some embodiments, the invention relates to an automated farming installation wherein the second vertically movable part comprises a conveyor belt actuatable to pour a load of substrate on the work surface.

Using a separate conveyor to receive and discharge one load of product to any level of work area allows to keep the mobile workstation within a reduced height, reducing the gap between two levels of work areas. Thus, the number of work areas is increased within a given height limitation.

By using a conveyor belt, the energy and the height of the conveyor necessary to pour the load of the product on one of the work areas is reduced.

According to some embodiments, the invention relates to an automated farming installation wherein the second vertically movable part comprises a base structure and a mobile carrier movable with respect to the base structure to an expanded position where it extends outside of the static structure to either receive or deliver substrate.

According to some embodiments, the invention relates to an automated farming installation wherein the lift system comprises an engine and a counterweight, and comprising a switching system alternately assembling and disassembling the first and the second vertically movable part to/from one another.

The counterweight is fixed on the other extremity to balance the weight of the vertically movable part, the mobile workstation, the conveyor and one load of product.

According to some embodiments, the invention relates to an automated farming installation further comprising a load relief system adapted to alternately assemble the vertically movable part to the static structure and disassemble it therefrom.

According to some embodiments, the invention relates to an automated farming installation wherein the vertically movable part comprises a base structure and a mobile workstation holder, and wherein the mobile workstation holder is movable with respect to the base structure within the vertically movable part.

According to some embodiments, the invention relates to an automated farming installation wherein there is one single mobile workstation.

According to some embodiments, the invention relates to an automated farming installation wherein the at least one mobile workstation is adapted to perform at least one or more of the following sub-actions:

- deliver one load of substrate from an entry module of the work surface;
- treat substrate at the work surface;
- move one load of substrate through an exit module of the work surface.

Thus, the manpower is reduced.

Thus, the product can be moved to an empty portion of the work surface far at the side of the installation opposite to the lift system.

Thus, the product can have the same thickness.

Thus, by repeating the same sub-action on each work area portion, we can collect all the product.

The movable workstation has a limit in terms of weight that it can unload. So, the portion of the work surface that can be unloaded of substrate is limited by the weight/volume of substrate the mobile workstation can move. Thus, to fully unload the automated farming installation with substrate, if the substrate weight is greater than the weight movable capacity of the mobile workstation, the unloading action is split into several unloading sub-action. Each of these sub-actions can be performed on a different portion of the work surface.

Thus, the substrate is brought to the next treatment phase of the whole cycle: sorting, or drying, or any other treatment phase requested after the second aging phase.

Thus, automatic insect culture is possible with very limited man action.

The substrate is for example a mix of insect larvae with nutrients, such as for example organic waste as collected from agricultural co-products, like in ethanol plants or breweries.

According to an example, the substrate is made of 4- or 5-days old larvae mixed with organic waste at the beginning of the second aging phase. At the end of the second aging phase, the substrate mainly comprises mature insects and frass. Some unprocessed organic waste remains. During the second aging phase, some actions have to be performed to achieve the substrate transformation.

Thus, the maximum substrate thickness supported by the horizontal tank can be loaded.

Thus, the yield of the said automated farming installation is increased.

Also, the ground footprint is optimized, and the yield is multiplied by the number of levels of work areas one under the other, without requesting investing into several additional mobile workstations.

Thus, the only remaining limitation regarding the size of the work surface is the time requested by the mobile workstation to operate over the whole work surface compared to the time limit to perform the operations.

The portion of the work surface that can be loaded with one product is limited by the weight/volume that the mobile workstation can move. Thus, to fully load the automated farming installation with one product, if the work surface capacity to receive product is higher than the load capacity of the mobile workstation, the loading action is split into several sub-actions of loading. Each of these sub-actions are performed on a different portion of the work surface. These sub-actions can be also repeated on the same portion of the work surface to increase the thickness of the product by adding a layer of product over previous layer(s) of product already loaded.

BRIEF DESCRIPTION OF THE DRAWINGS

Embodiments of the invention will be described below, in relation to the following drawings:

FIG. 1 shows a schematic simplified side view of an automated farming installation, with four 6-meter-long culture areas, one under the other, comprising a guiding chain carrier system comprising a compensation trolley mounted under a first level of one or several lowest units to assemble, the mobile workstation being at the operation location nearest the static connection point.

FIG. 2 shows the same schematic simplified side view of the same automated farming installation as FIG. 1, the mobile workstation being at the operation location furthest from the static connection point.

FIG. 3 shows a 3D detailed view of only the compensation trolley from a side and upper point of view.

FIG. 4 shows a 3D detailed view of the automated farming installation, the work area being cut and not completely displayed to give a better visual access to the guiding chain carrier system.

FIG. 5 shows a lateral view of a lift system and the mobile workstation in the air.

FIG. 6 is a perspective view of a unit according to one embodiment of the invention.

FIG. 7 is a sectional view of an embodiment of an output module.

On the drawings, the same reference signs show the same or similar objects.

DETAILED DESCRIPTION

This is a detailed description of one embodiment of the invention.

The automated farming installation 2 extends along a main longitudinal direction. On one side of the automated farming installation along the main longitudinal direction, an input module 13 is installed. On the opposite side, an output module 54 is installed. A cultivation module 14 is installed in between the input module 13 and the output module 54.

The cultivation module 14 comprises a plurality of work areas 3, also called culture areas 3, which are vertically superimposed to one another. For example, the first culture area 3 is installed about one meter above the ground X. The other culture areas 3 are positioned above the first culture area 3.

In this embodiment, all culture areas 3 are identical or similar. A given culture area 3 is disposed horizontally. It may comprise a single bed of a plurality of meter long, for example 6 meter long, for example 20 meter long, 50 meter long, or even longer than that, and of profiled cross-section.

The cultivation module 14 further comprises a vertical frame, not represented on FIG. 1, comprising vertical columns which are positioned on each longitudinal side of the beds at regular spacing, less than one meter for example, to support the weight of the culture areas 3. The vertical frame may further comprise linking components which assemble the vertical columns to one another on each longitudinal side of the tanks and/or the two longitudinal sides to one another. The vertical frame is positioned for example along the beds.

The structure of each culture area 3 comprises a rectangular plate which was shaped to provide a bed. Hence, the bed comprises a substantially flat bottom plate and the longitudinal edges of each culture area 3 have flanges 15 in order to retain the substrate 100 in the culture area 3. Each bed may thus also be called here a "tank". The lateral edges of each culture area 3 are flat to facilitate the loading and unloading of the substrate 100. Each culture area 3 is assembled to the vertical frame.

In the embodiment as shown on the FIGS. 1 and 2, guide rails 4 are positioned above each respective culture area. Guide rails extend longitudinally. For example, a guide rail is provided below the middle of the lower surface of the rectangular bottom plate portion of an overlying culture area 3 in this embodiment. A guide rail 4 is provided to guide the movement of a mobile workstation in relation to a culture area 3 below it, as will be discussed below.

In another embodiment, the guide rails 41 can be fixed on the columns of the automated farming installation 2 on each longitudinal side of the tank. According to yet another embodiment, two parallel guide rails 4 are provided overlying the culture area 3, and spaced laterally from one another. The guide rails 4 are parallel to the longitudinal edges of the culture areas. The guide rails 4 extend longitudinally and are straight.

The cultivation module is provided as a plurality of units, which are assembled one to another. FIG. 6 shows an example of a unit 44. Each unit 44 comprises at least a tank portion 45, at least a frame portion 46 allowing connection to at least one other unit, and at least a track portion 47. According to one embodiment, a unit 44 may comprise a plurality of tank portions 45 provided one above the other on a plurality of levels such as, for example, four levels, as shown (typically, one unit may be made of between one and ten levels). The unit 44 may comprise a plurality of track portions 47, in particular one track portion per tank portion. One track portion 47 may itself comprise a plurality of parallel rail portions, if a track is to be made of a plurality of rails. The frame portion 46 of one unit 44 can sustain several units above it. Further, it leaves an available space below a lowest first level of assembled units. Further, one or more units may be equipped with sensors and/or components of an air conditioning system.

In particular, a unit 44 may comprise vertical posts 48, for example four vertical posts which are provided as two pairs, with a pair of posts on each longitudinal side of the unit 44. The posts of a side pair of vertical posts may be assembled to one another by crossbars 49 or other structural elements.

The lateral structures may be connected with one another with crossbars 50 which extend from one longitudinal side to the other, and in particular from one vertical post to another. The crossbars 50 extend for example horizontally.

The vertical posts 48 comprise top and bottom connectors 51 to assemble the unit with an overlying and underlying, respectively, other unit.

The frame portion 46 may also comprise connectors 52 to assemble the unit with a neighbor unit. A neighbor unit is adjacent the considered unit in the longitudinal direction.

Connectors 51, 52 might be not necessary for end units, such as the lowest, the highest units, or units provided at each longitudinal end of the system.

For example, five units can be assembled one above the other. Up to 12 levels can be provided within a 8-meter-high facility. Further, along the longitudinal direction, a plurality of units, in particular from two to ten units, can be assembled one to another. The units are for example about 3-meter long, and they are connected to one another along their length.

Thus, on each level, the same number of units is assembled. However, in some cases, some levels may be provided as a different number of units, in order to accommodate to a specificity of the facility, for example.

The tank portion 45 of each unit is fixed to the frame portion 46. In particular, according to one example, as can be seen on FIG. 6, a tank portion is supported by the horizontal crossbars 50, and is fixed thereto by suitable fixation means.

Hence, each unit comprises at least one profiled portion of tank, whereby, upon assembly of units, at least one continuous profiled tank is provided by the sealed assembly of the individual portions of tank of the units. By "profiled", it is meant that the transverse cross-section of the tank is identical along the longitudinal direction of the tank. In particular, surrounding brackets may be provided, which are bolted below the tanks at the junction between the tank portions of two longitudinally neighbor units, so as to maintain the tank portions in fitted relationship. FIG. 6 shows a row of piercings at the longitudinal edges of the tank portion, which are designed to be assembled to the brackets.

If a tank portion of a unit is made of a plurality of longitudinally shorter tank components, they may be assembled to one another using a similar bracket 53 as shown on FIG. 6.

Each unit comprises a profiled track portion 47. The track portion 47 is shown here as comprising at least two parallel guiding rail portions. A guiding rail portion is for example fixed to the underside of the horizontal crossbars 50. Upon assembly of units, a continuous guiding rail is provided by the assembly of the individual portions of guiding rail of the units. A continuous track is provided by the assembly of the individual portions of guiding track of the units.

Thus, according to an invention, it is provided a module for an insect farming installation, where the module comprises a structural frame supporting a profiled tank portion, the module comprising a connection system adapted to connect the module to a neighbor module with a profiled tank portion, so that the tank portions of both modules form a continuous profiled tank portion. This invention therefore also relates to an assembly of modules for an insect farming installation, where each module comprises a structural frame supporting a profiled tank portion and a connection system adapted to connect the module to a neighbor module with a profiled tank portion, so that the tank portions of both modules form a continuous profiled tank portion.

A mobile workstation 6 is provided to perform one or more actions in the culture areas. Notably, the mobile workstation 6 is arranged to cooperate with the guiding track associated with a culture area in order to be moved along this guiding track. One lift system 5 can vertically lift the mobile workstation 6. The lift system 5 is installed at one lateral side of the culture areas 3, for example on the side of the input module 13. As will be described in more details below, the lift system comprises a static structure 32, such as a metallic frame, and a vertically movable part 23 movable vertically with respect to the static structure 32.

Notably, the lift system 5 may be either assembled to the mobile workstation 6 is order to be able to move the mobile workstation 6 vertically up and down, or unassembled in order to allow the mobile workstation 6 leaving the lift system and performing one or more actions in a culture area.

The input module further comprises a supply system 58 to supply the cultivation module with substrate to be cultivated.

The output module 54 is provided on the side of the installation opposite the input module. FIG. 7 shows an example of an output module 54. The output module 54 comprises, for each level, a ramp 55 which guides the unloaded substrate toward a bottom reception area 56. The bottom reception area 56 is below the level of the lowermost culture area 3, so as to receive the unloaded substrate from all levels. Gravity guides the unloaded substrate toward the reception area 56.

Because the unloaded substrate mainly comprises big fat insect larvae, according to one embodiment, one provides a braking system in order to slow down the substrate falling to the bottom reception area under the effect of gravity. The braking system may comprise a labyrinth. The labyrinth is designed so that the movement of the substrate in the labyrinth under the effect of gravity causes the substrate to be braked by the labyrinth surfaces.

According to one example, the braking system comprises ramps 55 from each culture area, and counter ramps 57 which are provided with a reverse slope with respect to the ramps 55. The counter ramps 57 have their ramp wall facing the direction of an overlying ramp 55, and the ramps 55 have their ramp wall facing the direction of an overlying counter ramp 57.

In this way, the unloaded substrate unloaded from top levels moves downward under the effect of gravity, but is braked by the alternated ramps and counter ramps met during their trajectory downward.

According to an aspect, one invention relates to an output module for an insect farming installation comprising a plurality of work areas the one above the other, where the output module comprises a common vertical column guiding the unloaded substrate toward a bottom reception area under the effect of gravity, and a braking system adapted to slow down the substrate during their movement downward.

As shown on FIG. 1, for example, a first engine installed on a mobile workstation 6 can move the mobile workstation 6 above a culture area 3. The mobile workstation 6 is connected to cables and pipelines. The cables and pipelines can be of three types:

- carrying energy, like electricity, compressed air,
- supplying products like water,
- exchanging digital data.

The mobile workstation 6 can be connected by an ethernet cable to send and receive data from and to a controller (not represented). The mobile workstation 6 is thus connected to the controller.

In the embodiment of FIG. 1 and FIG. 2, the mobile workstation has suspension wheels 11. In this position, the mobile workstation 6 is borne by the lift system 5. The lift system 5 for example has a static frame or structure 32, and a vertically movable part 23 adapted to move vertically with respect to the static frame. The vertically movable part 23 has a rail section 230. The vertically movable part 23 of the lift system can be moved vertically, and stopped in a position where the rail section 230 of the vertically movable part 23 is continuously facing the guide rail 4 of the cultivation module. Or, more precisely, in one embodiment, as will be described in more details below, the vertically movable part 23 can be stopped in a position where the rail section 230 can be placed facing the guide rail 4. The suspension wheels 11 of the mobile workstation 6 are positioned on the rail section 230 of the lift system 5. The lift system 5 positions the rail section 230 in continuity with the guide rails 4 corresponding to a culture area 3 selected by an operator or through a controller programmed by the operator to repeat cycles of movements of the mobile workstation.

A static connection area 7 may be located under the first culture area 3. The static connection area 7 may be provided at a vertical side of a wall where all the sockets alimented by these sources of energy, air, water, and data exchange are grouped. The position of the static connection area 7 is approximately halfway between the ground and the first culture area. The static connection area 7 is close to the lateral side of the culture areas where a lift system 5 is located. The static connection area 7 is oriented towards the opposite lateral side of the culture areas 3. Alternatively, there might be a plurality of static connection areas for various cables and/or pipelines.

Below the static connection area 7, there is a hole to let the guiding chain 20 pass horizontally.

The cables and pipelines are connected to the static connection area 7. The lengths of the said cables and pipelines are enough to let the mobile workstation 6 move to an operation location furthest away from the static connection area 7.

These cables and pipelines are guided by a 1-dimension guiding chain 20. The guiding chain 20 is made of numerous chain links of hollow parallelepiped structure connected to one another according to an axis of rotation. Each rotation axis is located close to one single side of the guiding chain 20. The minimum possible angle between two contiguous chain links without damaging the 1-dimension guiding chain 20 is 150°.

The maximum possible angle between two contiguous chain links without damaging the 1-dimension guiding chain 20 is 190°. All the rotation axis are parallel. Thus, flexibility operates essentially on only one side of the guiding chain 20. Thus, the final assembled guiding chain 20 is a corridor where cables and/or pipelines can be threaded.

The first extremity 21 of the 1-dimension guiding chain is fixed on the mobile workstation 6, on an axis fixed perpendicular of one lateral side of the mobile workstation. The second extremity 22 of the 1-dimension guiding chain 20 is fixed on the static connection area 7.

The 1-dimension guiding chain 20 is installed vertically in a position comprising several windings all oriented towards the only flexible side of the guiding chain 20. This position results of the interaction between the 1-dimension guiding chain 20 and three chain pulleys 10, 30, 40 positioned in the vertical plane defined by the 1-dimension guiding chain.

A compensation rail 9 is provided fixed under the culture area 3 closest to the ground X. A compensation trolley 8 comprises a structure 84, four sustaining wheels 12 and a pinion 82 interacting with a rack, and a second engine 81 able to apply a compensation force on the pinion 82.

The compensation trolley 8 comprises also the first chain pulley 10. The first chain pulley 10 is mounted on a longitudinal side of the compensation trolley 8, its axis of rotation is connected to the compensation trolley 8 by a lateral structure 83 comprising several rods and metal plate protruding on one longitudinal side of the compensation trolley 8. The height of the lateral structure 83 is below the diameter of the chain pulley 10 and the chain pulley 10 is mounted on this structure so as to extend both over and under this structure. Thus, once mounted on the automated farming installation 2, the guiding chain 20 is putting pressure on the structure 83. The structure 83 is more resistant to pressure force than to stretching force. To avoid any friction between the guiding chain 10 and the lateral structure 83, a supporting wheel 85 is added on the lateral structure 83, at the opposite side and at an upper position of the first chain pulley 10, on the lateral structure 83.

The compensation trolley 8 is keeping the orientation of the guiding chain 20 according to a U-turn configuration. The guiding chain 20 is starting horizontally from the static connection area 7, wrapping around the first chain pulley 10, horizontally and below the static connection area 7. The compensation trolley 8 is moving thanks to the sustaining wheels 12 supported on the compensation rail 9. The compensation trolley 8 comprises the second engine 81 applying a force to retain the movement of the compensation trolley 8 to maintain the guiding chain 20 straight. The compensation trolley 8 is connected to a source of electric energy by cables guided by a secondary guiding chain not represented. Retaining force is when the mobile workstation 6 is getting closer to the static connection area 7; the retaining force is reduced when the mobile workstation 6 is getting further from the static connection area 7. Thus, there is no folding and nor stretching of the guiding chain 20.

After passing between the ground X and the static connection area 7, the guiding chain 20 passes below the lift system 5 and reaches a second chain pulley 30 attached to the automated farming installation 2. The second chain pulley 30 is changing the orientation of the guiding chain 20 from horizontal to vertical. The second chain pulley 30 is vertically aligned with a third chain pulley 40. The third chain pulley 40 is attached to the vertical movable part of the lift system 5 comprising a support section able to support the mobile workstation 6. The third chain pulley 40 is changing the orientation of the guiding chain 20 from vertical to horizontal.

The lift system 5 can be controlled directly by the operator or through the controller programmed by the operator to repeat cycles of movements of the mobile workstation. The same mobile workstation 6 can thus operate on all the culture areas 3 by selecting one level of culture area 3, then another one.

As shown on FIG. 2, for example, after the operator has selected the fourth level, the lift system 5 reached the furthest position to work on the culture area 3.

The retaining force is applied on the guiding chain by the second engine 81 through the interaction between the pinion 82 and the rack. The retaining force to apply is calculated by the controller based on the values of the signals sent by or to the first engine.

The compensating system comprises a controller which is monitoring several signals and generates several command signals according to 3 different processes.

The first movement process, also named normal horizontal process, is described here below:

The initial phase is a blocked configuration wherein both first and second engines are blocked in rotation and the mobile workstation is at a standby position illustrated on FIG. 1.

First, the controller receives an order to move the mobile workstation 6 and to perform actions among several possible actions.

Second, the controller analyzes this information and calculates as a result a first command signal sent to the first engine.

Third, the first engine generates a first representative signal of its movement.

Fourth, when the controller receives the first representative signal, it generates a second command signal to the second engine 81. The intensity of the second command signal is calculated to move the compensating trolley 8 at half speed and opposite direction compared to the movement of the mobile workstation 6.

Fifth, the controller sends to the mobile workstation 6 a command signal to execute the actions.

Sixth, when the order is accomplished, the controller sends the order to move back the mobile workstation 6 and to stop the first engine and the second engine 81 in the initial standby position.

In the case the received command comprises a change of level, a second movement process is added twice in the horizontal process, before and after the fifth step of the normal horizontal process.

The second movement process, also named normal vertical process, is described here below:

The initial phase is when the mobile workstation is completely supported by the vertically movable part 23.

First, the controller receives an order to move the mobile workstation 6 to a different level of working area 3.

Second, the controller analyzes this information and calculates as a result a third command signal to a third engine 91 to move the vertically movable part 23 upward or downward, in the direction toward the required level.

Third, the third engine generates a third representative signal of its movement.

Fourth, when the controller receives the third representative signal, it generates a second command signal to the second engine 81. The second command signal intensity is calculated to move the compensating trolley 8 at half speed compared to the speed of the vertically movable part 23. The direction of the compensating trolley 8 is closer to the lift system 5 if the movement of the vertically movable part 23 is upward movement. The direction of the compensating trolley 8 is further away from the lift system 5 if the movement of the vertically movable part 23 is downward movement.

Fifth, the lift system 5 sends to the controller a command signal to indicate the level reached by the vertically movable part 23. When the initial level order is indicated as reached by the lift system 5 to the controller, the controller sends the order to stop and block the third engine and the second engine 81.

In the case of resistance force applied on at least one of the engines is over a normal range, a third movement process, also named emergency stop process, is launched as described here below:

First, the initial phase is when one of the first, second or(and) third engine(s) is(are) sending to the controller a resistance signal outside of the normal range.

Second, the controller immediately interrupts any ongoing movement command signal.

Third, the controller sends a signal to block all the engines.

Fourth, the controller activates a red light and generates an alarm sound.

According to FIG. 1, the mobile workstation 6 comprising four sustaining wheels 11 is located on the lift system 5, at the level of the first culture area.

Not visible on the figures, a flexible security cable made of steel is following the same path as the guiding chain 20. The end points of the security cable are fixed to the same elements as the extremities 21, 22 of the guiding chain 20. The length of the security cable is slightly shorter than the guiding chain 20. This difference of length between the security cable and the guiding chain 20 is not enough to generate any folding of the guiding chain 20. Nevertheless, when a tension force appears, it is largely supported by the security cable instead of the guiding chain 20.

The chain pulleys are positioned on one longitudinal side of the compensation trolley and on one longitudinal side of the mobile workstation. The said longitudinal sides are the sides parallel to the direction of movement of the mobile workstation.

The path segments followed by the guiding chain comprises several longitudinal lengthwise cases for storing the guiding chain 20.

For supporting the weight of the guiding chain 20, a longitudinal lengthwise case 90 is fixed on the automated farming installation 2, as illustrated on FIG. 4. The said longitudinal lengthwise case 90 is holding the guiding chain between the first chain pulley 10 and the second chain pulley 30. Similar longitudinal lengthwise case, not represented, is fixed on the automated farming installation to hold the guiding chain between the third pulley 40 and the mobile workstation 6.

The controller keeps the information of the current location reached by the mobile workstation 6. The controller receives an instruction comprising a dedicated level of work area 3.

If the mobile workstation 6 is not on the vertically movable part 23, the instruction is kept in the memory of the controller in a row of standby instructions. If the mobile workstation 6 is not yet at the level corresponding to the dedicated work area 3, the controller first launches the normal vertical process.

When the mobile workstation 6 is at the level of the work area 3 selected, the controller launches a first normal horizontal process. The direction of the first normal horizontal process is toward the side opposite to the side where the lift system 5 is set up.

The automated farming installation 2 sends a first detection signal when the mobile workstation has reached the opposite end of the work area 3. When the controller receives the first detection signal, the controller stops the first normal horizontal process and launches a second normal horizontal process. The direction of the second normal horizontal process is opposite to the first normal horizontal process.

When the mobile workstation is completely back on the vertically movable part 23, a second detection signal is sent to the controller. When the controller receives this second detection signal, the controller stops the second normal horizontal process. In case there is not another instruction in standby, the controller launches a normal vertical process in the direction to the lowest work area 3.

During a second aging phase cycle, these three movement processes are combined. During the first movement process, the controller also activates, in parallel, one of the functions available at the level of the mobile workstation to perform several cycles of the second aging phase one after the other.

Each second aging phase cycle lasts few days, for example 7 to 8 days.

After a maturation of BSF eggs until the larvae hatch and for a first aging phase for a few days in a nutrient made of organic waste, the initial substrate 100 is ready. A second aging phase of the initial substrate 100 in tank lasts for 7 to 8 days, resulting in a final substrate 100 mainly made of the non-nutritive fibers, mature larvae of BSF and frass.

The invention is addressing this second aging phase, which can be split into 4 main sub phases: one first sub-phase of loading substrate 100, one second sub-phase of warming and treating the substrate 100, one third sub-phase of cooling and treating the substrate 100 and one fourth sub-phase of unloading substrate 100.

The functions available at the mobile workstation are loading, treating and unloading the substrate 100. A conveyor (not represented) may also be linked to the mobile workstation. The conveyor has only lateral walls to retain the substrate 100 and to allow loading and unloading the substrate 100.

On each culture area 3, the substrate 100 is loaded and unloaded respectively at the beginning and at the end of one second aging phase cycle.

At the beginning of one second aging phase, the operator 200 launches the sub phase of loading substrate 100.

Initially, the mobile workstation 6 is at a standby position, vertically at the lowest level, and on the lift system 5. The supply system 58 is for example provided so as to provide substrate from the side of the lift system opposite to the side facing the work surface 3. Substrate 100 is loaded on the conveyor until it reaches its loading limitation (step 1). In this embodiment, the capacity is limited to a part of the working surface, for example the equivalent of one meter long of substrate 100 of one work area 3. One load of substrate is for example about 30 kg.

Then, the substrate is supplied by the supply system on the nearest part of the mobile workstation 6.

Then, the controller launches the first mobile workstation 6 movement process: normal horizontal process until reaching the opposite end of the working area 3 minus one portion, for example one meter (step 2).

During step 3, the controller launches also the action of loading the substrate 100 to the appropriate position in the culture area. This function can be ensured by the action of pressurized air to actuate mechanical pushers and other tools (rake for instance) of the mobile workstation 6.

When the substrate 100 is loaded over the appropriate length (for example one meter, which is one exemplary distance) of the lowest work surface 3, the tools are stopped by the controller, and the normal horizontal process is completed by the return of the mobile workstation to the standby position (step 4).

Steps 1 to 4 are repeated. At each occurrence, the horizontal normal process at step 2 is reduced by the previously filled length of the working area until the lowest work area 3 is completely filled with substrate 100.

Then, step 1 is repeated, followed by the second movement process: the normal vertical process (step 5) in the upward direction until reaching the highest level of the working area 3. Then, the steps 2 and 3 are performed, then the normal vertical process in the downward direction is launched by the controller until the mobile workstation 6 is back to its standby position (step 6).

Steps 1, 5, 2, 3, 6 and 4 are repeated in this order. At each occurrence, the horizontal normal process at step 2 is reduced by one meter until the higher work area 3 is completely filled with substrate 100.

Then, the vertical movement upward (step 5) and downward (step 6) are reduced by one vertical level.

Then, steps 1, 5, 2, 3, 6 and 4 are repeated in this order. At each occurrence, the horizontal normal process (step 2) is reduced by the length of the previously loaded portion of the culture area, until one of the work areas 3 above the lowest working surface 3 is completely filled with substrate 100.

Then, the vertical movements, upward (step 5) and downward (step 6), are reduced by one vertical level, followed by the same cycles (steps 1, 5, 2, 3, 6 and 4) repeated with step 2 reduced by one meter at each occurrence until one of the work area 3 is completely filled with substrate 100.

Then, the reduction of the vertical movement, upward (step 5) and downward (step 6), followed by the same cycles is repeated until all the work areas 3 are filled with substrate 100.

Once the substrate 100 is in place on all the work areas 3, some steps of treating the substrate can be repeated as needed during the 7 days of the cycle to perform other actions. These actions are performed by activating different actuators of the mobile workstation 6. These actions may be launched based on a predetermined schedule.

The second aging phase usually lasts 7 to 8 days. When the operator decides that the larvae (i.e. BSF) have reached maturity, he launches the substrate removal process. For example, the mobile workstation 6 is at a standby position, vertically at the lowest level, and on the lift system 5.

Then, the controller launches the first movement process: normal horizontal process until reaching the work area 3 without substrate 100 minus one meter (step 2').

The first occurrence of step 2' on one given level is reaching the opposite end of one work area 3 minus one meter.

Then the pushers are activated by the controller (step 2"). This function is ensured by the action of pressurized air at the level of pushers. Then the normal horizontal process is applied to move over the remaining surface until reaching the opposite side edge of the tank, pushing one meter long of substrate 100 out of the work area 3 to a reception area 56, for example into a collecting bin of the output module (step 2'"). Then, the normal horizontal process is launched in the opposite direction until reaching a position of the work area 3 corresponding to a length of substrate to be unloaded (step 3').

Steps 2', 2", 2'" followed by 3' are repeated until the lowest work area 3 is empty (cycle 1).

Then the second movement process is applied by the controller: the normal vertical process (step 5') in the upward direction until reaching the highest level of the work area 3.

Then, the steps 2', 2", 2'" and 3' are repeated until the work area 3 is empty (cycle 1).

Then, the normal vertical process in the downward direction is launched by the controller until the mobile workstation reached the next level (step 5').

Then, cycle 1 followed by step 5' is repeated until the lowest work area 3 is empty.

Thus, all the substrate 100 is pushed out of the work surface 3. This is the end of one second aging phase cycle. As soon as one second aging phase cycle is achieved, another second aging phase cycle can be launched. A cleaning phase between two second aging phase cycles can be added.

On a same automated farming installation, each horizontal level can also have a different independent cycle than the cycles of the other horizontal levels.

On one embodiment, to position the mobile workstation precisely at the entrance of each work area, as shown on FIG. 5, the vertically movable part 23 is provided with a mobile workstation holder 24, which is adapted to hold the mobile workstation 6 in two positions. The mobile workstation holder 24 comprises for example a structure such as a rectangular frame equipped with an engine (not shown) able to move the mobile workstation 6 with respect to the structure. For example, the movement of the mobile workstation 6 with respect to the structure is a translation movement along an axis which is inclined with respect to the vertical. The inclination axis is for example less than 45°. For example, four links 25 are integral with the rectangular frame, oriented in the same direction and with the same angle. The links have oblong holes 26 in the middle of each link, adapted to receive guided devices 27, such as wheels, linked to the mobile workstation 6. Thus, the engine can move the mobile workstation 6 up and down according to an oblique direction, getting closer to the work area 3 in the lowest position. The mobile workstation holder 24 is vertically moved within the lift system from a position one level above the lowest level of work area up to one level above the highest level of work area. During this vertical movement, the mobile workstation 6 is in the up position with respect to the mobile workstation holder 24, close to the rectangular frame.

The mobile workstation holder 24 further comprises a load relief system 28. The load relief system may comprise one or more arms 29 which are provided movable with respect to a main structure 31 of the mobile workstation holder. One or more engines (not shown) may be provided to move the arms with respect to the main structure 31. The arms 29 may be moved with respect to the main structure 31 between an expanded position, as shown on FIG. 5, and a retracted position. In the retracted position, the arms 29 do not interfere with the static structure 32 of the lift system 5 upon vertical movement of the vertically movable part 23. In the expanded position, the arms 29 expand with respect to the main structure 31, so that they would interfere with the static structure 32 upon a vertical movement of the vertically movable part 23.

The mobile workstation holder 24 and the mobile workstation 6 move together vertically. When the mobile workstation holder 24 reaches a level associated to an intended work by the workstation 6, the arms 29 are moved to their extended position where they can interact with the static structure 32. For example, the arms 29 in this position rest on the static structure 32. The load of the mobile workstation holder 24 is thus supported directly by the static structure 32. Thus, the group of the mobile workstation holder 24 and the mobile workstation 6 are stabilized in a fixed vertical position configuration. Once in a fixed vertical position configuration, the mobile workstation 6 is moved with respect to the mobile workstation holder 24. The mobile workstation 6 is moved down along the links until it is facing the guide rail 4. FIG. 5 shows an intermediate position. A guiding system may be provided to precisely align the mobile workstation 6 with the rail 4, so as to cope with the low precision of the positioning by the lift system. This guiding system may for example be based on male cones positioned ahead of the mobile workstation holder 24 which are blocked by female cones (not illustrated) at one entrance edge of each work area. Thus, the mobile workstation 6 may be stopped before it reaches the end of its movement track with respect to the mobile workstation holder 24. Thus, the wheels 11 of the mobile workstation 6 are precisely aligned with the track of each work area.

The mobile workstation 6 can thus be controlled to be moved along the track, whereby it is disassembled from the vertically movable part 23.

When the mobile workstation 6 finishes working at this work area, it is assembled to the lift system 5 according to a reverse order of the above steps. The mobile workstation 6 is first moved back to cooperate with the rail section 230 of the vertically movable part 23. The mobile workstation 6 is moved up toward the main structure 31, and the arms are moved to their retracted position, so that the vertically movable part 23 can be moved to another level. It should be noted that, according to this embodiment, it is not compulsory to use the load relief system 28. This embodiment may alternatively be used with the vertically movable part 23 suspended in the lift.

According to one embodiment, the lift system is built as described below. The vertically movable part 23 is assembled to a lifting cable 33. A counterweight 34 movable vertically is also assembled to the lifting cable. When the vertically movable part 23 is on the topmost possible position, which is one level above the highest work area, the counterweight 34 is still suspended thanks to a set of pulleys 35. Thus, the balance ensured by the counterweight is ensured whatever the vertical position of the top frame is. The lift system engine can move the cable.

According to one embodiment, the lift system 5 is also used to supply with substrate material. In this embodiment, the lift system 5 comprises a second vertically movable part 36. The second vertically movable part 36 is movable vertically within the static structure. For example, the second vertically movable part 36 is below the first vertically movable part 23, and will remain below the vertically movable part 23 throughout operation of the system.

The lift system 5 comprises an engine to move the second vertically movable part 36. According to one example, the same engine is used to either move the first vertical movable part or the second vertically movable part. According to this embodiment, the lift system is built as described on FIG. 5. The second vertically movable part 36 is assembled to the lifting cable 33. The lift system 5 comprises a control switch adapted to control the assembly of the first vertical movable part with the second vertically movable part. In a first configuration, the first vertical movable part is assembled to the second movable vertical part, so that the two parts may be moved vertically together. In particular, when, as described above, the first vertically movable part 23 is supported directly by the static structure 32 of the lift system 5, it is possible to disassemble the second vertical movable part 36 from the first vertical movable part. The second vertically movable part 36 may be used to move substrate vertically in the lift system, in order for the substrate to be distributed to the culture area 3.

By default, the position of the second vertically movable part 36 is at the bottom of the lift system 5 and the first vertically movable part 23 is assembled to it and located just above it. According to one embodiment, as shown, the second vertically movable part 36 comprises a base structure 38 and a mobile carrier 39 adapted to move with respect to the base structure 38. In particular, as shown, the mobile carrier 39 may be controlled to move horizontally with respect to the base structure, between a compact position, where the second vertically movable part 36 can be moved vertically, and an expanded position, where the mobile carrier 39 expands partly outside of the static structure 32 of the lift system, thereby preventing the second vertically movable part 36 from being moved vertically. In particular, in the expanded position, the mobile carrier 39 may be placed under a substrate supply system 58. For example, this movement is allowed only at one level of the lift system, for example, the bottommost level. For example, the expanded position is at the rear of the lift system 5, i.e. on the side of the lift system opposite to the work areas. According to yet another embodiment, the mobile carrier 39 may also take another expanded position, where part of the mobile carrier 39 extends above a culture area. This eases the transfer of substrate from the mobile carrier 39 to the culture area 3 by the mobile workstation 6. For example, this other expanded position may be reached only at the levels of the lift system corresponding to a culture area, but not at the bottommost level.

According to yet another embodiment, which may be integrated with the ones above, the mobile carrier 39 may comprise a base 42 and an endless conveyor belt 43 borne by the base 42. The endless conveyor belt 43 surrounds the base 42, serves as a support for the substrate, and maybe actuated so as to convey the overlying substrate toward a given direction. The endless conveyor belt 43 may be actuated, when receiving substrate from the substrate supply system 58, as shown on FIG. 5, to move so that substrate can be supplied to the whole surface of the mobile carrier 39 without moving the substrate supply system 58. In addition or alternately, the endless conveyor belt 43 may be actuated to convey the substrate from the mobile carrier 39 toward and into the culture area 3. The mobile workstation 6 will then be used to convey the substrate from the entry of the culture area 3 to the relevant linear portion thereof, as described above.

When the second vertically movable part 36 is filled with substrate, it is moved vertically along with the first vertically movable part 23 assembled thereto. When the second vertically movable part 36 is placed level with the culture area to be filled, and the mobile workstation 6 is located just above it, the mobile workstation 6 may be operated to transfer the substrate from the second vertically movable part 36 into the culture area 3, as described above. If the first vertically movable part 23 is supported by the lift structure, as described above, and the second vertically movable part 36 is empty of substrate, the two vertically movable part are disassembled from one another. The second vertically movable part 36 is moved downward in order to be filled with substrate due to fill another level, as described above. This corresponds to the configuration of FIG. 5. Meanwhile, the mobile workstation 6 operates at the level which has just been filled with substrate. Once the second vertically movable part 36 is filled with substrate, it is moved vertically upward until it assembles to the first vertically movable part 23. The first vertically movable part 23 then is disassembled from the lift structure. The two vertically movable parts 23, 36 are then moved together to another level where substrate is to be dealt.

If no substrate is to be dealt, the first vertically movable part 23 is displaced from level to level where the mobile workstation 6 through moving the second vertically movable part to which it is assembled.

Thus, according to an invention, it is provided an input module for an insect farming installation having culture areas on a plurality of overlying levels, and comprising a lift system to move a mobile workstation and/or substrate to the levels.

Further variations of the subject of the invention by exchanging individual features among themselves or for equivalents and combinations thereof fall within the scope of the present invention.

LIST OF REFERENCES

2 automated farming installation
3 work area/Culture area
4 guide rails
5 lift system
6 mobile workstation
7 static connection area
8 compensation trolley
9 compensation rail
10 chain pulley
11 suspension wheels
12 sustaining wheel
13 input module
14 cultivation module
15 flanges
20 guiding chain 21 first extremity
22 second extremity
23 vertically movable part
24 mobile workstation holder
25 links
26 oblong hole
27 guided device
28 load relief system
29 arm
30 chain pulley
31 main structure
32 static structure
33 Cables
34 counterweight
35 pulley
36 second vertically movable part
38 base structure
39 Mobile carrier
40 chain pulley
41 guide rails
42 base
43: conveyor belt 44 unit
Tank portion 45 Frame portion 46 Track portion 47 Vertical posts 48 Crossbars 49
Crossbars 50
Connectors 51 Connectors 52
Bracket 53 Output module 54 Ramp 55 Reception area 56
Counter ramps 57 Supply system 58
81 second engine
82 pinion 83 lateral structure
84 structure
85 supporting wheel
90 lengthwise case
91 third engine 100 substrate
200 operator
230 rail section

The invention claimed is:

1. An automated farming installation, wherein the automated farming installation comprises a controller, at least one mobile workstation controlled by the controller, and at least one work surface able to support at least a load of substrate, wherein the work surface comprises a longitudinal continuous tank made by connection of at least two profiled tank portions, and in that the mobile workstation is movable over a portion of the work surface to perform at least one sub-action controlled by the controller,
- wherein the automated farming installation comprises at least two work surfaces provided at least two vertical levels, the one under the other,
- and the automated farming installation further comprises a lift system comprising:
  - a static structure,
  - a vertically movable part, vertically movable with respect to the static structure, and adapted to receive, to support and to deliver the mobile workstation.

2. The automated farming installation as claimed in claim 1, further comprising a structural frame supporting the work surface, wherein the farming installation is provided as a plurality of assembled units, each unit comprising one of said tank portions and a structural frame portion, the structural frame portions being assembled to one another to provide the structural frame.

3. The automated farming installation as claimed in claim 1, further comprising at least one longitudinal guiding rail parallel to the longitudinal continuous tank and guiding a movement of the mobile workstation over the work surface.

4. The automated farming installation as claimed in claim 2, further comprising at least one longitudinal guiding rail parallel to the longitudinal continuous tank and guiding a movement of the mobile workstation over the work surface, and wherein each unit comprises a rail portion, the rail portions being assembled to provide the longitudinal guiding rail.

5. The automated farming installation according to claim 2, comprising at least two work surfaces provided at least two vertical levels, the one under the other, and wherein at least one of the units comprises at least the two vertical levels.

6. The automated farming installation according to claim 2, wherein at least one of the units is adapted to support at least an overlying unit.

7. The automated farming installation as claimed in claim 1, wherein the lift system further comprises a second vertically movable part, vertically movable with respect to the static structure.

8. The automated farming installation as claimed in claim 7, wherein the second vertically movable part comprises a conveyor belt actuatable to pour a load of substrate on the work surface.

9. The automated farming installation as claimed in claim 7, wherein the second vertically movable part comprises a base structure and a mobile carrier movable with respect to the base structure to an expanded position where it extends outside of the static structure to either receive or deliver substrate.

10. The automated farming installation as claimed in claim 7, wherein the lift system comprises an engine and a counterweight, and comprising a switching system alternately assembling and disassembling the first and the second vertically movable part to/from one another.

11. The automated farming installation as claimed in claim 1, further comprising a load relief system adapted to alternately assemble the vertically movable part to the static structure and disassemble it therefrom.

12. The automated farming installation as claimed in claim 10, wherein the vertically movable part comprises a base structure and a mobile workstation holder, and wherein the mobile workstation holder is movable with respect to the base structure within the vertically movable part.

13. The automated farming installation as claimed in claim 1, wherein there is one single mobile workstation.

14. The automated farming installation as claimed in claim 1, wherein the at least one mobile workstation is adapted to perform at least one or more of the following sub-actions:

deliver one load of substrate from an entry module of the work surface;

treat substrate at the work surface;

move one load of substrate through an exit module of the work surface.

* * * * *